(12) United States Patent
Britt et al.

(10) Patent No.: US 11,714,066 B2
(45) Date of Patent: Aug. 1, 2023

(54) SELF-CALIBRATING ANALYTE SENSOR

(71) Applicant: MATRIX SENSORS, INC., San Diego, CA (US)

(72) Inventors: David K Britt, El Cerrito, CA (US); Paul R Wilkinson, El Segundo, CA (US); Steven Yamamoto, San Diego, CA (US)

(73) Assignee: MATRIX SENSORS, INC, San Diego, CA (US)

( * ) Notice: Subject to any disclaimer, the term of this patent is extended or adjusted under 35 U.S.C. 154(b) by 126 days.

(21) Appl. No.: 17/470,748

(22) Filed: Sep. 9, 2021

(65) Prior Publication Data

US 2022/0082525 A1   Mar. 17, 2022

Related U.S. Application Data

(60) Provisional application No. 63/077,527, filed on Sep. 11, 2020.

(51) Int. Cl.
*G01N 29/036* (2006.01)
*G01N 27/22* (2006.01)
*G01K 11/26* (2006.01)
*F25B 21/04* (2006.01)
*G01N 33/00* (2006.01)

(52) U.S. Cl.
CPC ........... *G01N 29/036* (2013.01); *F25B 21/04* (2013.01); *G01K 11/26* (2013.01); *G01N 27/223* (2013.01); *G01N 33/004* (2013.01); *G01N 2291/014* (2013.01); *G01N 2291/021* (2013.01)

(58) Field of Classification Search
CPC .. G01N 29/036; G01N 27/223; G01N 33/004; G01N 2291/014; G01N 2291/021; G01N 2291/0255; G01N 2291/0256; G01N 2291/0423; G01N 2291/0426;
(Continued)

(56) References Cited

U.S. PATENT DOCUMENTS 6,202,480 B1 * 3/2001 Mauze ................... G01N 25/64
73/64.45
8,056,394 B2   11/2011 Frerichs
(Continued)

*Primary Examiner* — Francis C Gray
(74) *Attorney, Agent, or Firm* — Mark B. Floyd

(57) ABSTRACT

A sensor device comprises at least one transducer and a sensing material disposed on the transducer. The sensing material adsorbs or absorbs an amount of analyte (e.g., a target gas) that depends on a temperature of the sensing material and a concentration of the analyte. At least one detector is arranged to measure responses of the transducer to sorption or desorption of the analyte in the sensing material while the sensing material is heated and/or cooled according to at least one temperature profile. The device also comprises a humidity sensor that is arranged to detect a humidity level of the environment or sample containing the analyte. A processor or controller is programmed to determine the quantity (e.g., concentration) of the analyte by comparing values of the transducer measurement signals to reference data indicative of expected or pre-measured responses of the transducer to known concentrations of the analyte at the same humidity level as indicated by the humidity sensor while the sensing material is subjected to the same or similar temperature profile.

13 Claims, 3 Drawing Sheets

(58) Field of Classification Search
CPC .. G01N 29/022; G01N 29/2406; F25B 21/04; G01K 11/26
See application file for complete search history.

(56) References Cited

U.S. PATENT DOCUMENTS

| | | |
|---|---|---|
| 8,265,881 B1 | 9/2012 | Lakhotia et al. |
| 9,007,593 B2 | 4/2015 | Sailor et al. |
| 2009/0293590 A1* | 12/2009 | Zeng .................... G01N 29/022 73/24.06 |
| 2017/0184556 A1 | 6/2017 | Toffoli et al. |
| 2018/0202961 A1* | 7/2018 | Sussner ................. A61B 5/055 |
| 2019/0033275 A1 | 1/2019 | Sun |
| 2019/0072523 A1* | 3/2019 | Britt ...................... G01N 29/036 |
| 2019/0219543 A1* | 7/2019 | Gilmore ................. G01N 29/36 |
| 2020/0207606 A1 | 7/2020 | Bulgurcu Bilgen et al. |

\* cited by examiner

SELF-CALIBRATING ANALYTE SENSOR

CROSS REFERENCE TO RELATED APPLICATIONS

This application claims the benefit of U.S. provisional patent application 63/077,527 filed on Sep. 11, 2020 hereby incorporated by reference in its entirety.

BACKGROUND

The invention relates generally to sensors for detecting substances, and in particular to a sensor for monitoring the presence or quantity of an analyte (e.g., a target gas) in an environment or sample.

Chemical sensing of gases is an important technology in several fields including environmental monitoring, industrial safety, and public security. Depending on the application and target gas, different operating principles have been deployed, ranging from electrochemical, metal-oxide semiconductor, and non-dispersive infrared absorption. One approach to a scalable gas sensor is a solid-state device based on a sensing material applied as a coating to a resonant mass transducer.

A first problem to overcome is that resonant chemical sensors can be highly sensitive to other gases including even moderate changes in relative humidity. When measuring an analyte in ambient environmental conditions, the sensor indicates not only a mass change due to the presence of a target gas, but also due to the additional adsorption of water molecules in the sensing material. While many sensing materials can be tailored to detect specific analyte molecules, the absorption of water molecules is a more difficult problem to solve due its omnipresence and chemical activity.

A second problem is that sensors in general, and gas sensors in particular, are known to drift over time. The drift mechanism varies with technology, but generally is caused by consumption of material (electrochemical), degradation of optical components, degradation of sensing material, or thermally-induced changes in readout electronics. For example, optical carbon dioxide sensors require periodic manual calibration (e.g., every 6 to 12 months) to compensate for long term drift. In a conventional calibration procedure, a sensor is exposed to a known concentration of the target gas and the output signal is adjusted—so-called "baseline calibration". Additionally, the sensitivity may also be calibrated by exposing the sensor to several concentrations and adjusting both the baseline (or offset) as well as the slope of the response (or sensitivity). This conventional calibration process is an expensive and invasive procedure, but foregoing this procedure can result in sensors that no longer operate within their advertised performance specifications.

Gas sensors (e.g., $CO_2$ sensors) are currently deployed for monitoring indoor air quality to ensure adequate ventilation and as a component of demand-controlled ventilation systems. However, current optical $CO_2$ sensors are costly and prone to long-term drift, which requires manual recalibration about every six months. A low-cost sensor not requiring manual calibration would enable an expanded deployment of demand-controlled ventilation and indoor air quality monitoring.

There is still a need for a simple, low cost sensor to detect analyte that overcomes the problems of drift, humidity and water adsorption by the sensing material.

SUMMARY

A sensor device is provided for determining a quantity of at least one analyte (e.g., a target gas) in an environment or sample with correction for the effects of humidity. The device comprises at least one transducer (e.g., a resonant mass transducer). A sensing material is disposed on the transducer, and the sensing material has an ability to adsorb or absorb an amount of the analyte that depends on a temperature of the sensing material and a concentration or partial pressure of the target gas. At least one detector is arranged to detect responses of the transducer to sorption or desorption of the analyte in the sensing material and to output transducer measurement signals indicative of the responses of the transducer (e.g., frequency shifts). At least one thermal element is arranged to heat and/or cool the sensing material according to at least one temperature profile (e.g., a temperature ramp, temperature sweep, temperature step or thermal cycle). Optionally, the device includes at least one temperature sensor to measure a temperature of the sensing material and to output temperature measurement signals. The device further comprises at least one humidity sensor arranged to detect a humidity level of the environment or sample containing the analyte (e.g., target gas) and to output at least one humidity measurement signal.

At least one processor or controller communicates with the detector, the temperature sensor and the humidity sensor to receive the transducer measurement signals, temperature measurement signals, and humidity measurement signals. The processor is programmed to determine the quantity (e.g., concentration) of the analyte from the received signals or data indicative of the transducer responses, the humidity level, and optionally the measured temperature of the sensing material. The transducer responses to a changing temperature of the sensing material are compared to reference data. In some embodiments, the reference data comprises pre-measured response curves or data sets indicative of responses of the transducer to sorption or desorption of the analyte in the sensing material (e.g., gas uptake) for a range of known concentrations of the analyte pre-measured at the same humidity level as indicated by the humidity sensor while the sensing material was subjected to substantially the same temperature profile. The previously measured responses of the transducer (or a substantially equivalent transducer) may be in the form of a plot (or curve), or may be tabulated data (e.g. lookup table). In other embodiments, the reference data may be in the form of a mathematical model that predicts the transducer responses under known chemical environments (e.g., known concentrations or partial pressures of the analyte and known humidity levels).

According to another aspect, a method is provided for determining a quantity of at least one analyte (e.g., a target gas) in an environment or sample with correction for the effects of humidity. The method comprises the step of heating and/or cooling a sensing material disposed on a transducer according to at least one temperature profile. The sensing material has an ability to adsorb or absorb an amount of the analyte that depends on a temperature of the sensing material and a concentration or partial pressure of the analyte. The method also comprises the steps of detecting responses of the transducer to sorption or desorption of the target gas in the sensing material as its temperature is changed, and outputting transducer measurement signals indicative of the responses of the transducer. The method further comprises the step of utilizing at least one humidity sensor to measure a current humidity level of the environment or sample. Optionally, a temperature sensor is utilized to measure the temperature of the sensing material as it is heated and/or cooled. At least one controller or processor is utilized to determine the quantity of the analyte from the transducer measurement signals and the measured humidity level by comparing the transducer responses to a changing temperature of the sensing material to reference data. In some embodiments, the reference data comprises pre-measured response curves or data sets indicative of responses of the transducer to sorption or desorption of the analyte in the sensing material (e.g., gas uptake) for a range of known concentrations of the analyte pre-measured at the same humidity level as indicated by the humidity sensor while the sensing material was subjected to substantially the same temperature profile. The previously measured responses of the transducer (or a substantially equivalent transducer) may be in the form of a plot (or curve), or may be tabulated data (e.g. lookup table). In other embodiments, the reference data may be in the form of a mathematical model that predicts the transducer responses under known chemical environments (e.g., known concentrations or partial pressures of the analyte and known humidity levels).

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. An element includes one or more elements. Any recitation of an element is understood to refer to at least one element. A plurality of elements includes at least two elements. Unless otherwise required, any described method steps need not be necessarily performed in a particular illustrated order. A first element (e.g., a signal or data) derived from a second element encompasses a first element equal to the second element, as well as a first element generated by processing the second element and optionally other signals or data. Making a determination or decision according to (or in dependence upon) a parameter encompasses making the determination or decision according to the parameter and optionally according to other signals or data. Unless otherwise specified, an indicator of some quantity/data may be the quantity/data itself, or an indicator different from the quantity/data itself such as a signal from which the quantity/data can be determined.

Transducers detect substances by using a sensing material that adsorbs or absorbs an analyte (e.g., molecules of a target gas such as $CO_2$). The sorption of the gas molecules in the sensing material changes properties that are reflected in a mechanical or electromechanical response of the transducer (e.g., a frequency shift). Resonant mass transducers are sensitive to small amounts of water vapor even at moderate levels of relative humidity. When monitoring a target gas in ambient conditions, the transducer responses may indicate uptake (e.g., a mass change) in the sensing material not only due to the target gas, but also due to the additional adsorption of water molecules in the sensing material. This disclosure provides devices and methods that overcome the inaccuracy or interference in sensing target gas caused by water vapor or other interfering substances in the sensing material.

Figure 1:
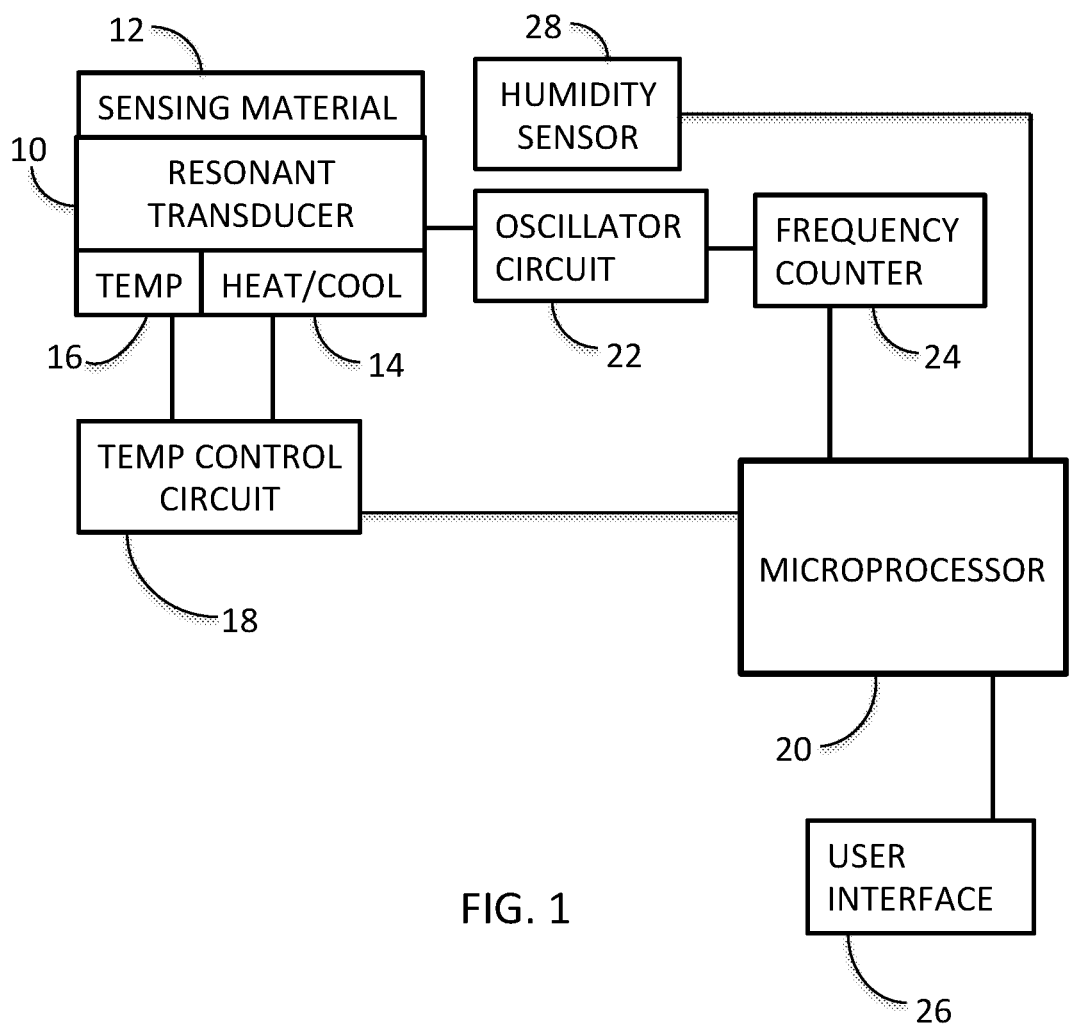
FIG. 1 is a block diagram of a sensor device that varies temperature of a sensing material to determine analyte concentration according to a first embodiment of the invention.

FIG. 1 shows a schematic block diagram of a device for determining the quantity (e.g., concentration) of an analyte (e.g., a target gas such as $CO_2$). The device comprises a sensing material 12 that adsorbs or absorbs the target gas, if present in the environment or sample to which the device is exposed. The sensing material has an ability to adsorb or absorb an amount of the target gas that depends on a temperature of the sensing material and a concentration or partial pressure of the target gas. Partial pressure as used herein is interchangeable (synonymous) with the gas concentration, not ambient or atmospheric pressure. The sensing material 12 is disposed (e.g., coated) on a transducer 10. In preferred embodiments, the transducer is a resonant mass transducer such as a quartz crystal microbalance (QCM), surface acoustic wave (SAW) transducer, cantilever or a capacitive micromachined ultrasonic transducer (CMUT). The gas uptake (e.g., mass loading due to sorption and desorption of the target gas) in the sensing material 12 is monitored by a change in the transducer frequency, quality factor, stiffness, strain or a combination of these parameters.

In some embodiments, the sensing material 12 is a porous coordination polymer (PCP), and most preferably a type of PCP known as a metal-organic framework (MOF) material. Other suitable sensing materials include, but are not limited to: polymer films and metal-oxides. In some examples, the sensing material 12 is from a family of porous metal-organic framework materials known as amine-appended $M_2$(DOBPDC). Such materials exhibit characteristic gas uptake behavior that varies with temperature and the concentration of the target gas (e.g., $CO_2$). In particular, the material mmen-$Mg_2$ (DOBPDC) exhibits an impressive 14 weight percent $CO_2$ uptake with a sharp mass uptake step that depends on temperature and the concentration of $CO_2$.

At least one thermal element 14 is positioned to heat and/or cool the sensing material 12. The thermal element 14 is arranged to heat and/or cool the sensing material 12 according to at least one temperature profile. In some embodiments, the temperature profile is a simple temperature ramp from room temperature (e.g., 25° C.) to a predetermined maximum temperature (e.g., 90° C.). In other examples, the temperature profile is a temperature sweep, step or a more complex thermal cycle.

The term "thermal element" means at least one heater, cooling element, or device that provides both heating and cooling. For example, in some embodiments, the thermal element is simply a resistive heater, and passive cooling is used. In other embodiments, the thermal element is an active cooling element. In still other embodiments, the thermal element provides both active heating and cooling, in which case the thermal element 14 is preferably a thermoelectric device (TED) that heats and cools the sensing material 12. In general, suitable heating elements include conductive heaters, convection heaters, or radiation heaters. Examples of conductive heaters include resistive or inductive heating elements, e.g., resistors or thermoelectric devices. Convection heaters include forced air heaters or fluid heat-exchangers. Suitable radiation heaters include infrared or microwave heaters. Similarly, various cooling elements may be used to cool the sensing material 12. For example, various convection cooling elements may be employed such as a fan, Peltier device, refrigeration device, or jet nozzle for flowing cooling fluids. Alternatively, various conductive cooling elements may be used, such as a heat sink (e.g. a cooled metal block) or cooling fins.

Optionally, at least one temperature sensor 16 is arranged to measure a temperature of the sensing material 12. In some embodiments, the temperature sensor 16 is integral with the thermal element 14, for example there are some heaters (e.g., resistive heaters) that also perform temperature sensing by measuring an electric property of the heater circuit, as is known in the art. Alternatively, the temperature sensor 16 may be a separate element from the thermal element 14 (e.g., the temperature sensor 16 may be a thermistor). In some embodiments, the temperature sensor comprises a mechanical resonator having at least two resonant modes with different, known temperature dependencies. In some embodiments, the first and third harmonics are used to determine temperature. An example of using a resonator (e.g., QCM) to determine temperature is given in the publication "Sensing of Organic Vapor Adsorption on Gold Using a Temperature Insensitive Microbalance" by Kim & Pierce, 1999 Joint Meeting EFTF—IEEE IFCS, pages 1001-1004.

A temperature control circuit 18 is preferably connected to the thermal element 14 and a microprocessor 20. The temperature control circuit 18 operates under control of the microprocessor 20 to heat and/or cool the sensing material 12 according to the temperature profile. The temperature profile may be pre-programmed (e.g., stored in memory of the microprocessor 20) or user-selected. The temperature sensor 16 is optional and not required because the temperature profile may be executed by controlling the thermal element 14 without measuring temperature. More preferably, the temperature sensor 16 is included in the device and connected in a temperature control feedback loop with the thermal element 14, temperature control circuit 18, and the microprocessor 20. Many suitable temperature control feedback loops are known in the art. Preferably, the resolution of the temperature control system is less than 1° C., and more preferably the resolution is less than or equal to 0.1° C. for more precise temperature control and measurements.

The position of the thermal element 14 and temperature sensor 16 (which may be integral with the thermal element 14 in some embodiments) with respect to the transducer 10 and the sensing material 12 may be different for different embodiments and applications of the sensor device. For example, FIG. 1 shows an embodiment in which the thermal element 14 and the temperature sensor 16 are positioned on the backside of the resonant transducer 10 (e.g., a QCM), with the sensing material 12 disposed (e.g., coated, deposited or grown) on the topside of the transducer 10. This is a convenient arrangement of parts when the transducer is a QCM having topside and backside electrodes positioned on opposing sides of a quartz substrate. The thermal element 14 and temperature sensor 16 are preferably a resistive heater and a thermistor positioned on the backside of the QCM, and the sensing material 12 (e.g., a MOF) is positioned on the topside of the QCM (e.g., disposed over the top electrode of the QCM).

In many embodiments, the action of heating/cooling the transducer 10 and measuring the temperature of the transducer 10 is sufficient to also heat/cool the sensing material 12 and measure the temperature of the sensing material 12, since the sensing material 12 will be at the same temperature as the transducer 10. It is not necessary to have direct physical contact between the sensing material 12, the thermal element 14 and the temperature sensor 16. So long as there is adequate thermal contact between these elements of the device, the temperature sensor 16 positioned on the backside of the transducer 10 will be at nominally the same temperature as the sensing material 12, and heat will be able to flow from the thermal element 14 through the transducer 10 to the sensing material 12. In an alternative embodiment (not shown), the thermal element 14 and the temperature sensor 16 are positioned between the sensing material 12 and the top side of the resonant transducer 10.

The sensor device also includes at least one detector (e.g., a readout circuit for a resonant mass transducer) arranged to detect responses of the transducer 10 when substances (e.g., molecules of the target gas and/or water molecules) are adsorbed or absorbed in the sensing material 12. The readout circuit outputs transducer measurement signals indicative of the transducer responses. In a preferred embodiment, the transducer is a resonant mass transducer (e.g., a QCM), the transducer responses to mass changes in the sensing material 12 are frequency shifts, and the detector is a readout circuit comprising an oscillator circuit 22 that drives the transducer 10 and a frequency counter 24 that measures the frequency (e.g., resonance frequency or frequency shifts). Many suitable oscillator circuits and frequency counters are known in the art. The oscillator circuit 22 and the frequency counter 24 output the transducer measurement signals (e.g., frequency signals from the frequency counter 24) to the microprocessor 20.

Although a QCM is the presently preferred transducer, the oscillator circuit 22 and the frequency counter 24 are the preferred detector, and frequency signals are the presently preferred "transducer measurement signals", there are many other suitable transducers, detection mechanisms for those transducers, and transducer measurement signals output from those detectors that are known in the art. Transducer responses that may be detected and output as transducer measurement signals include a change in frequency, resonance frequency, dissipation, quality factor, stiffness, or strain. The responses of the resonant transducer to mass loading in the sensing material are often detected using an electrical property, such as a change in impedance of the circuit driving an oscillating motion of the transducer 10.

Many electrical detection methods are known in the art to detect transducer responses to a change in uptake (i.e., sorption and desorption) of the target gas in the sensing material for a resonant mass transducer, or an array of transducers, and to output transducer measurement signals indicative of the transducer responses. In some embodiments, an optical detector is used to detect deflection or frequency shifts of the transducer 10. In other embodiments, the transducer 10 is an electronic element such as a resistor or a capacitor, and the sorption of mass in the sensing material 12 is monitored by a change in the transducer device resistivity, capacitance, or other electrical property. In other embodiments, many other types of transducers may be used, such as a calorimeter having the sensing material. In the calorimeter embodiment, the transducer measurement signals are indicative of heat evolved or consumed in the sensing material due to the adsorption or desorption, respectively, of the target gas.

At least one humidity sensor 28 is arranged to detect a humidity level of the environment or sample containing the analyte (e.g., target gas) and to output humidity measurement signals. Many suitable humidity sensors are known in the art. In some embodiments, the humidity sensor comprises a capacitor having a dielectric material that adsorbs and desorbs water, thus changing the capacitance between two electrodes and indicating the humidity level by capacitance measurement. U.S. Pat. No. 10,436,737 to Sussner et al. shows an example of a suitable humidity sensor comprising a capacitor having two electrodes and a MOF material positioned between the electrodes. In an alternative embodiment, the humidity sensor comprises two resonance sensors, one coated with hydrophobic material and the other coated with hydrophilic material, as described in US patent application 20150177196 published Jun. 25, 2015. Other suitable humidity sensors, such as a Sensirion SHT-85, are commercially available.

The microprocessor 20 is connected to the frequency counter 24, the temperature sensor 16, and the humidity sensor 28 to receive the transducer measurement signals/data, temperature measurement signals/data, and humidity measurement signals/data. These signals/data comprise inputs to the processor 20, and the processor uses an algorithm(s) to convert these signals/data into a numerical quantity (e.g., concentration) of the analyte. An optional user interface 26 is connected to the processor 20. The user interface 26 preferably includes a display for displaying a quantity of the target gas (e.g., concentration, mass or partial pressure), speakers or other mechanisms for sounding an alarm at certain gas concentrations, and at least one user-input mechanism for selecting parameter values.

The microprocessor 20 is programmed to determine the quantity (e.g., concentration) of the analyte in the sample or environment from the received signals or data. The transducer responses to sorption and desorption of the analyte in the sensing material as its temperature is changed (according to the temperature profile) is compared to reference data. In some embodiments, the reference data comprises previously measured responses of a substantially equivalent (or the same) transducer and substantially equivalent (or the same) sensing material under known chemical environments (i.e. known concentrations of the analyte, known humidity levels, and known temperature profile). The pre-measured responses may be in the form of a plot (or curve), or the pre-measured responses may be tabulated data (e.g. lookup table). In alternative embodiments, the reference data is provided by a mathematical model that predicts expected responses of the transducer under known chemical environments (concentrations of the analyte, humidity levels, and temperature profile).

The comparison between the measured responses of the transducer (indicated by the values of the transducer measurement signals) and the reference data may be made using any of the following methods:
1) A statistical comparison, such as the coefficient of determination, denoted $R^2$ or $r^2$ and pronounced "R squared". The statistical comparison may also be made using Chi-Squared or Analysis of variance (ANOVA).
2) A geometric comparison, such as Hausdoff distance, Frechet distance, or the Kologarov Smirnov statistic.
3) A correlation-based technique, such as cross-correlation.
4) A curve fit and comparison of the fit parameters to the pre-measured fit parameters at multiple chemical environments (concentrations and humidity levels).
5) A machine learning method that infers the concentrations of interest based on suitably chosen training sets.
6) A threshold measurement where the temperature at which a value of the transducer measurement signal crosses a threshold is compared and correlated to known values for the environment of the sensor device.

In some embodiments, the microprocessor 20 is programmed to determine the quantity (e.g., concentration) of the analyte in the sample or environment from the received signals or data by comparing a response curve of transducer responses to analyte sorption and desorption (e.g., gas uptake) in the sensing material 12, as a function of time or temperature, to pre-measured response curves. The pre-measured response curves are indicative of transducer responses to analyte sorption and desorption in the sensing material 12, as a function of time or temperature, for known concentrations of the analyte pre-measured at the same humidity level as indicated by the humidity sensor 28 while the sensing material 12 was subjected to substantially the same temperature profile. Thus, the quantity of the analyte is determined by varying the temperature according to the pre-determined temperature profile and measuring the transducer responses (e.g., gas uptake in the sensing material). This curve (gas uptake vs. temperature) is called an "isobar" curve.

Figure 2:
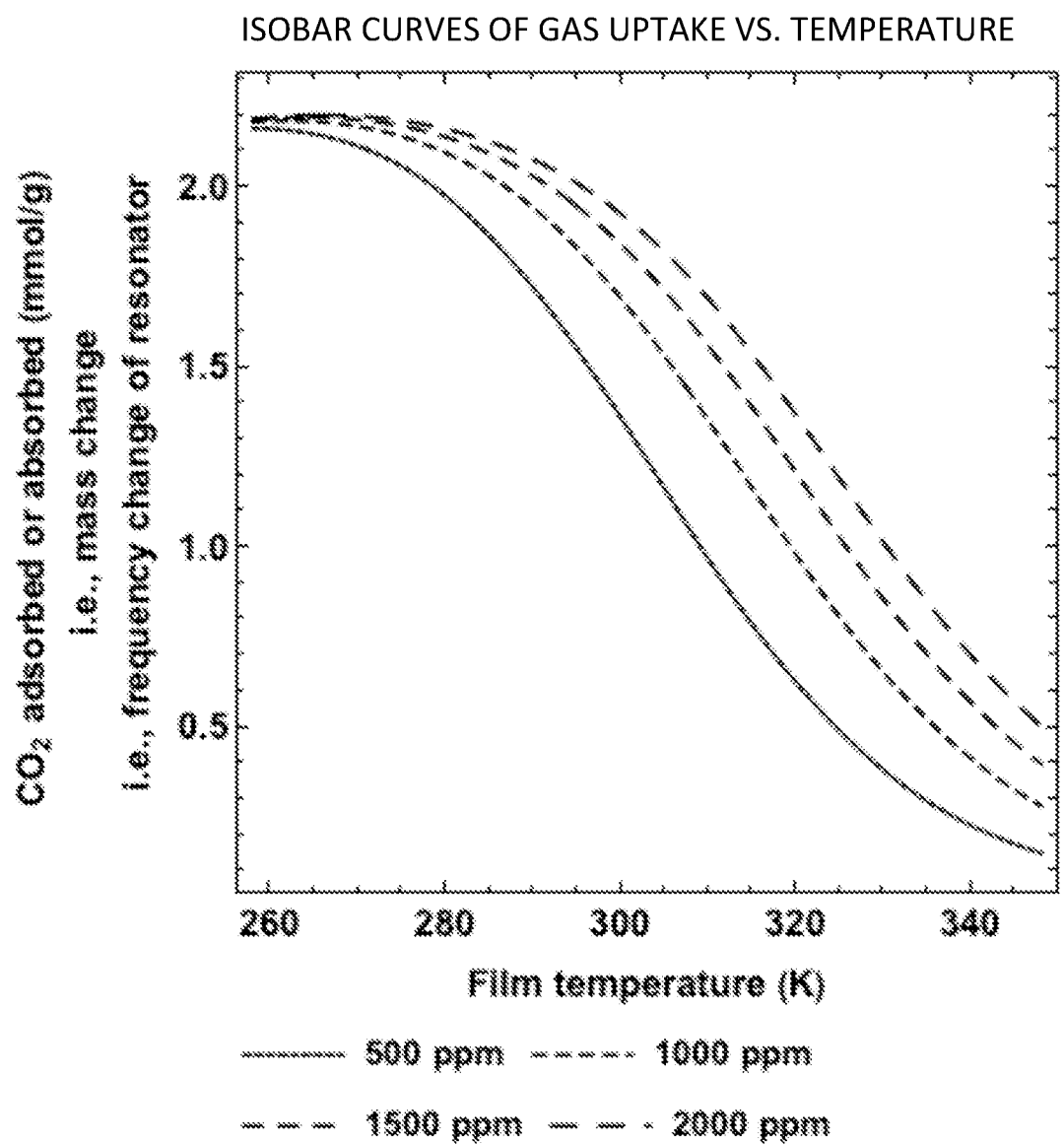
FIG. 2 is a graph illustrating isobar curves of sorption of analyte (e.g., gas uptake) in a sensing material vs. temperature, with four isobar curves at four different gas concentrations.

FIG. 2 is a graph illustrating isobar curves of sorption of analyte (e.g., gas uptake) in a sensing material vs. temperature. Each isobar is a unique curve (shape and position) that corresponds to a specific gas concentration in the ambient environment. In this example, the graph illustrates sorption (gas uptake in mmol/g) of carbon dioxide in a film of MOF sensing material vs. temperature of the MOF sensing material. The graph shows four examples of isobar curves at four different gas concentrations (500 ppm, 1000 ppm, 1500 ppm, and 2000 ppm).

The sensor device is likely to encounter various different humidity levels on different days of operation. Varying humidity levels may affect the shape of the isobar curves because water vapor adsorbs into the sensing material. To compensate for humidity, isobar curves are pre-measured at various humidity levels, over a range of possible gas concentrations at each humidity level, and stored in the memory of the microprocessor. Because the current humidity level (e.g., relative humidity or absolute humidity) is measured by the humidity sensor, the correct gas concentration is determined by varying the temperature of the sensing material according to the pre-determined temperature profile, measuring the gas uptake (indicated by the transducer measurement signals) as the temperature is changed, and comparing the response curve of measured gas uptake to the pre-measured isobar curves at the appropriate humidity level indicated by the humidity sensor.

Examples of a suitable temperature profile include a temperature ramp, a temperature sweep, one or more temperature steps, or a more complex thermal cycle. In a first simple example of operation, the temperature prolife is a temperature ramp wherein the sensing material 12 is heated by the thermal element 14 from room temperature (e.g., 25° C.) to a pre-determined maximum temperature (e.g., 90° C.). In another embodiment, ramping the temperature in both directions (i.e. sweeping with rising temperature and dropping temperature) may enable the correction of hysteretic effects. In some embodiments, the sweeps are optimized for time, e.g. sweep quickly until identifying a region of interest, then slow down or reverse for a particular temperature range, and then continue. In alternative embodiments, a simplified architecture may be achieved with a temperature profile that is a temperature step. Instead of ramping the temperature up and down, heating is achieved by simply turning on the intended amount of heat and measuring what is nominally an exponential rise in the transducer measurement signal with the stepped temperature increase.

Note that it is possible to practice the device and method of this disclosure without technically drawing curves. In some embodiments, the sensor device utilizes signals/data such as signal values indicating transducer responses, temperature signals/data, and humidity signals/data. In some embodiments, it is useful to compare a response curve (indicating responses of the transducer to analyte sorption/desorption as temperature is changed) to reference data (e.g., pre-measured responses or predicted responses). The pre-measured responses may be in the form of a plot (or curve), or may be tabulated data (e.g. lookup table). The term "curve" is intended to mean a curve defined by, derived from, or fitted to the values of the signals or data. In some embodiments, the curve may be defined by the signal values by plotting the signal values vs. temperature. Or the curve may be derived from the signal values. In some embodiments, the gas uptake is proportional or sometimes inversely proportional to the signal values. In some embodiments, a response curve may be fitted to the signal values vs. temperature or time using any number of curve fitting algorithms. In some embodiments, the quantity is determined (e.g., calculated) by interpolation between pre-measured curves. Further, a curve may be compared to a lookup table, either directly or by interpolating the response between the pre-measured curves, the endpoints of which are curves or lookup tables determined at two known conditions.

Self-calibration of the sensor device is an important advantage. It is anticipated that the sensor device will not require manual calibration over its lifetime (e.g., 10 years). In some modes of operation, the sensor device may be used to monitor gas concentration in the manner of a conventional sensor by calculating analyte quantity from one or more transducer measurement signals using a traditional calibration curve or look-up table (e.g., stored in the memory of the microprocessor). However, sensors in general, and gas sensors in particular, are known to drift over time. The drift mechanism varies with technology, but generally is caused by consumption of material (electrochemical), degradation of components, or degradation of sensing material. The sensor of the present disclosure overcomes this problem because it is capable of self-calibration.

To perform a baseline self-calibration, the sensor device needs to know the ambient gas concentration to which the sensing material is being exposed. The correct gas concentration is determined by varying the temperature of the sensing material according to the pre-determined temperature profile, measuring the gas uptake (indicated by the transducer measurement signals) as the temperature is changed, and comparing the response curve of measured gas uptake to the database of isobar curves pre-measured at the humidity level indicated by the humidity sensor. Each isobar is a unique curve (shape and position) that corresponds to a specific gas concentration in the ambient environment, so that an accurate gas concentration can be determined with negligible or reduced effects of drift. Once this gas concentration is known, then an offset parameter is adjusted in software to "re-zero" the baseline used by the sensor device during conventional modes of operation to monitor gas. If this test is performed at several concentrations (e.g., at night with low $CO_2$ levels and in the middle of the day with high $CO_2$ levels because there are people present), then the slope or sensitivity of the output signal can also be self-calibrated.

In an alternative embodiment, the sensor device has a pressure source for varying the pressure of the sensing material while holding its temperature substantially constant. The processor is programmed to determine the quantity of the analyte from the received signals or data by comparing a response curve of gas uptake in the sensing material, as a function of time or pressure, to pre-measured response curves. The pre-measured response curves are indicative of gas uptake in the sensing material, as a function of time or pressure, for known concentrations of the analyte pre-measured at the same humidity level as indicated by the humidity sensor while the sensing material was subjected to substantially the same pressure profile. Thus, the quantity of the analyte is determined by varying the pressure according to the pre-determined pressure profile and measuring the transducer responses indicative of gas uptake in the sensing material. This curve (gas uptake vs. pressure) is called an "isotherm" curve.

Figure 3:
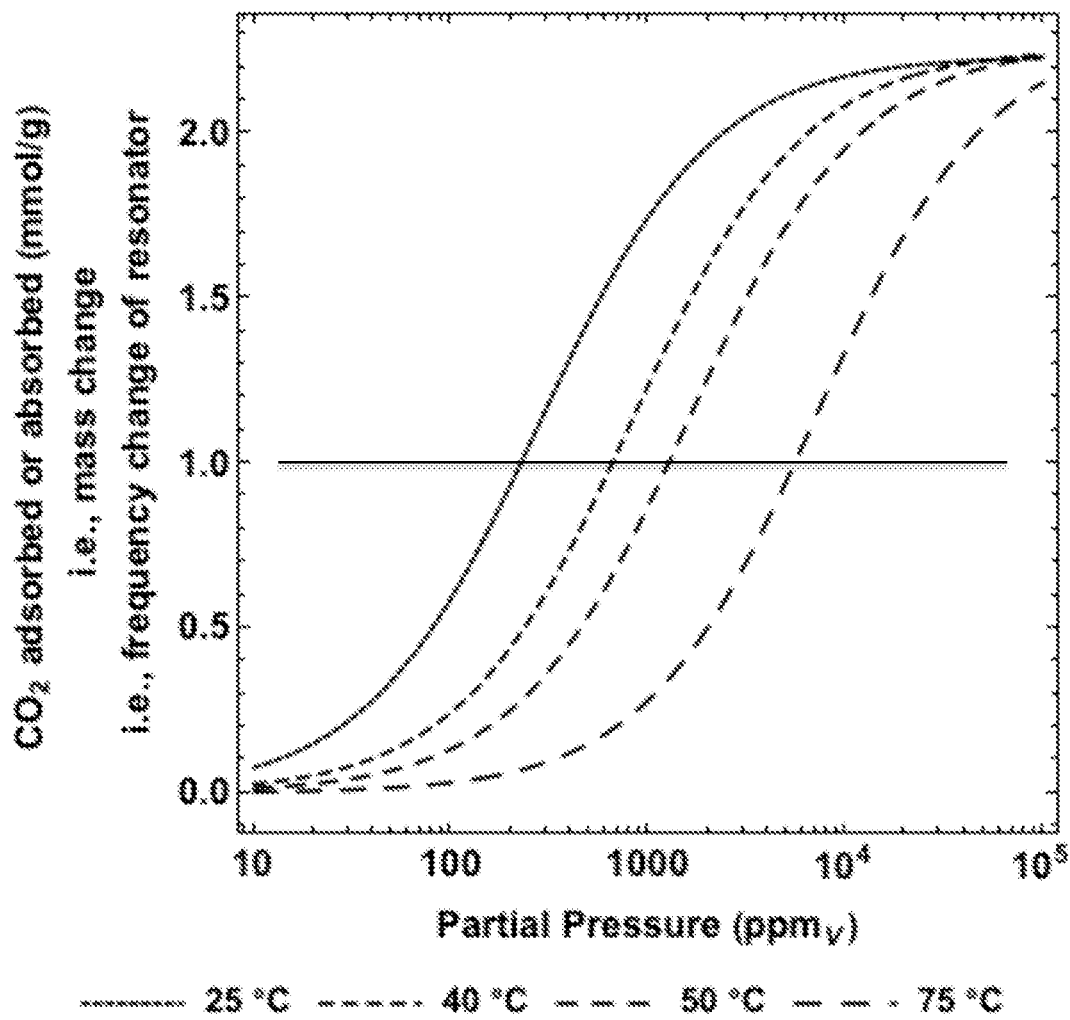
FIG. 3 is a graph illustrating isotherm curves of sorption of analyte (e.g., gas uptake) in a sensing material vs. pressure, with four isotherm curves at four different temperatures.

FIG. 3 is a graph illustrating isotherm curves of sorption of analyte (e.g., gas uptake) in a sensing material vs. pressure. Each isotherm is a unique curve (shape and position) that corresponds to a specific gas concentration in the ambient environment. The graph shows four examples of isotherm curves at four different temperatures (25° C., 40° C., 50° C. and 75° C.).

The above description illustrates embodiments of the invention by way of example and not necessarily by way of limitation. Many other embodiments are possible. For example, only one sensor element was shown at a time for simplicity of understanding in the patent drawings, but arrays of sensor devices are also possible in alternative embodiments. Arrays of transducers may be functionalized with MOFs or sensing materials having different properties so that the sensor array can sensitively detect and differentiate multiple target analytes, chemical compounds, and even complex mixtures. More generally, this could be a dual mode sensor for Analyte A and a second Analyte B, where Analyte B can be water (i.e. humidity).

In some embodiments, the sensor device includes at least one pressure sensor for sensing the ambient or atmospheric pressure. The ambient or atmospheric pressure should not be confused with the partial pressure of a target gas, which term partial pressure we are using as synonymous with the concentration of the target gas. An ambient pressure sensor may be useful for applications of the sensor device in which the ambient or atmospheric pressure may differ from standard atmospheric pressure, and adjustments to the calculation of the concentration of the target gas may include ambient pressure measurements.

In some embodiments, the controller or processor may include program instructions to alert another device or external computer that there is an alarm at a target concentration. For example, an alarm signal is set that can be communicated to another system such as a building ventilation control system. The target concentration for an alarm can be user-selectable by inputting through the user interface 26 a desired alarm concentration. One skilled in the art will recognize that the target concentration for the alarm signal may be selected in a variety of ways, such as factory settings or from another device or computer system communicating with the sensor device.

Although the above embodiments describe mmen-$Mg_2$(DOBPDC) or amine-appended $M_2$(DOBPDC) as a sensing material, the disclosure is not limited to these materials. Many other suitable sensing materials may be used in alternative embodiments such as other MOFs, polymers or metal-oxides (MOS). In general, a sensing material for $CO_2$ should exhibit at least 0.1 wt % uptake of $CO_2$ across the active sensor range (e.g., 400 to 2,000 ppm).

According to some embodiments, the present invention provides, inter alia, computer systems comprising hardware (e.g. one or more processors and associated memory) programmed to perform the methods described herein, as well as computer-readable media encoding instructions to perform the methods described herein. In some embodiments, pre-measured calibration curves or calibration data are used to determine the quantity (e.g., concentration, partial pressure, or mass) of each substance of interest (e.g., $CO_2$), according to the signals or data indicating the transducer responses (e.g., frequencies). The calibration curves or calibration data may be in one or more processors and associated memory included with the sensor device. In some embodiments, an on-board microprocessor is programmed to store measured signal values and/or to determine gas quantities or values. Alternatively, these functions may be performed in a separate processor or external computer in communication with the sensor portion of the device, with or without wires. Wireless communication between devices is well known in the art.

In other embodiments, the sensor has only some signal processing electronics, and some determination and calculation functions are performed in a separate processor or external computer in communication with the sensor. Alternatively, multiple processors may be provided, e.g., providing one or more signal processing electronics or microprocessors in the sensor that communicate (wirelessly or with wires) with one or more external processors or computers.

Although a single controller or processor is described in the above embodiments for simplicity in patent drawings, it is to be understood that the sensor device may include multiple processors and/or associated memories. In some embodiments, at least one on-board microprocessor receives transducer measurement signals/data, humidity measurement signals/data, and temperature measurement signals/data from the detector, humidity sensor, and the temperature sensor, respectively, either through direct connections or indirectly through one or more additional signal processing circuits or processor components. Similarly, the temperature control circuit 18 is described as a separate component for clarity of patent drawings, but is not necessarily a separate component. A temperature control circuit could be part of the one or more microprocessors.

Accordingly, the scope of the invention should be determined by the following claims and their legal equivalents.

What is claimed is:

1. A sensor device for determining a quantity of at least one analyte in an environment or sample with correction for the effects of humidity, the device comprising:
   a) at least one transducer;
   b) a sensing material disposed on the transducer, wherein the sensing material has an ability to adsorb or absorb an amount of the analyte that depends on a temperature of the sensing material and a concentration of the analyte;
   c) at least one thermal element arranged to heat and/or cool the sensing material according to at least one temperature profile;
   d) at least one detector arranged to detect responses of the transducer to sorption or desorption of the analyte in the sensing material as its temperature is changed according to the temperature profile and to output transducer measurement signals indicative of the responses of the transducer;
   e) at least one humidity sensor arranged to measure a current humidity level of the environment or sample and to output at least one humidity measurement signal; and
   f) at least one controller arranged to receive the transducer measurement signals from the detector and the humidity measurement signal from the humidity sensor, wherein the controller is programmed to determine the quantity of the analyte by comparing values of the transducer measurement signals to reference data indicative of expected or pre-measured responses of the transducer to known concentrations of the analyte at the same humidity level as indicated by the humidity sensor while the sensing material was subjected to substantially the same temperature profile.

2. The device of claim 1, wherein the transducer is a resonance sensor, and the detector measures at least one property indicative of the frequency of the resonance sensor.

3. The device of claim 1, wherein the sensing material comprises a metal-organic framework.

4. The device of claim 1, wherein the processor is programmed to compare the transducer measurement signals to reference data by comparing a response curve indicative of the responses of the transducer to sorption or desorption of the analyte in the sensing material, as a function of temperature or time, to pre-measured response curves.

5. The device of claim 4, wherein the response curve comprises an isobar curve indicative of the responses of the transducer to sorption or desorption of the analyte in the sensing material as its temperature is changed according to the temperature profile, and the pre-measured response curves comprise isobar curves pre-measured at the humidity level indicated by the humidity sensor while exposing the sensing material to known concentrations of the analyte.

6. The device of claim 1, wherein the controller is further programmed to adjust at least one calibration value of the sensor device utilizing the quantity of the analyte determined.

7. The device of claim 1, wherein the controller is further programmed to repeat the determination of the quantity of analyte when environmental conditions are different and to adjust at least one calibration slope value of the sensor device utilizing the quantities determined.

8. The device of claim 1, wherein the humidity sensor comprises a capacitor having a dielectric material that sorbs and desorbs water, thus changing the capacitance between at least two electrodes to indicate the humidity level.

9. The device of claim 1, further comprising at least one temperature sensor arranged to detect the temperature of the sensing material, wherein the controller is arranged to receive temperature signals from the temperature sensor, and the controller is further programmed to control the thermal element to initiate heating or cooling of the sensing material to execute the temperature profile.

10. The device of claim 9, wherein the temperature sensor comprises a mechanical resonator having at least two resonant modes with different temperature dependencies.

11. A method for determining a quantity of at least one analyte in an environment or sample, the method comprising:
   a) changing the temperature of a sensing material disposed on at least one transducer, wherein the sensing material has an ability to adsorb or absorb an amount of the target gas that depends on a temperature of the sensing material and a concentration of the target gas;
   b) detecting responses of the transducer to sorption or desorption of the target gas in the sensing material as its temperature is changed according to at least one temperature profile;
   c) outputting transducer measurement signals indicative of the responses of the transducer;

d) utilizing at least one humidity sensor to measure a current humidity level of the environment or sample; and e) utilizing at least one controller to determine the quantity of the analyte from the transducer measurement signals by comparing signal values to reference data indicative of expected or pre-measured responses of the transducer to known concentrations of the analyte at the same humidity level as indicated by the humidity sensor while the sensing material was subjected to substantially the same temperature profile.

12. The method of claim 11, wherein the controller compares the transducer measurement signal values to reference data by comparing a response curve indicative of the responses of the transducer to sorption or desorption of the analyte, as a function of temperature or time, to pre-measured response curves.

13. The method of claim 12, wherein the response curve comprises an isobar curve indicative of the responses of the transducer to sorption or desorption of the analyte in the sensing material as its temperature is changed according to the temperature profile, and the pre-measured response curves comprise isobar curves pre-measured at the humidity level indicated by the humidity sensor while exposing the sensing material to known concentrations of the analyte.

* * * * *